(12) United States Patent
Starobinets et al.

(10) Patent No.: US 12,731,501 B2
(45) Date of Patent: Sep. 8, 2026

(54) METHOD AND SYSTEM FOR DATA ACQUISITION PARAMETER RECOMMENDATION AND TECHNOLOGIST TRAINING

(71) Applicant: KONINKLIJKE PHILIPS N.V., Eindhoven (NL)

(72) Inventors: Olga Starobinets, Newton, MA (US); Sandeep Madhukar Dalal, Winchester, MA (US); Ekin Koker, Cambridge, MA (US); Saifeng Liu, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/692,356

(22) PCT Filed: Sep. 12, 2022

(86) PCT No.: PCT/EP2022/075280
§ 371 (c)(1),
(2) Date: Mar. 15, 2024

(87) PCT Pub. No.: WO2023/046513
PCT Pub. Date: Mar. 30, 2023

(65) Prior Publication Data

US 2025/0069515 A1 Feb. 27, 2025

Related U.S. Application Data

(60) Provisional application No. 63/247,380, filed on Sep. 23, 2021.

(51) Int. Cl.
*G09B 5/02* (2006.01)
*G16H 30/40* (2018.01)
*G16H 40/20* (2018.01)

(52) U.S. Cl.
CPC ............... *G09B 5/02* (2013.01); *G16H 30/40* (2018.01); *G16H 40/20* (2018.01)

(58) Field of Classification Search
CPC ......... G09B 5/02; G16H 440/20; G16H 30/40
See application file for complete search history.

(56) References Cited

U.S. PATENT DOCUMENTS 8,449,301 B2 * 5/2013 Cyr ...................... G09B 23/286 434/262
9,501,627 B2 * 11/2016 Reicher ................. G16H 30/20
(Continued)

FOREIGN PATENT DOCUMENTS

EP 3706035 A1 9/2020
WO 2020043610 A1 3/2020

OTHER PUBLICATIONS

International Search Report and Written Opinion Dated Jan. 20, 2023 For International Application No. PCT/EP2022/075280 Filed Sep. 12, 2022.
(Continued)

*Primary Examiner* — Xuan M Thai
*Assistant Examiner* — Sadaruz Zaman

(57) ABSTRACT

A non-transitory computer readable medium (**26*s*) stores instructions executable by at least one electronic processor (14*s*) to perform an operator assistance method (100) including: obtaining data related to reference imaging examinations during performance of the medical imaging examinations; generating training materials (32) from the obtained data; the training materials being related to the performance of the reference medical imaging examinations; and providing training user interface (UI) (44) on a display device (36), the training UI displaying a visualization (36**) of a selected
(Continued)

36 portion of the training materials which is selected based on information about a current or upcoming medical imaging examination.

20 Claims, 5 Drawing Sheets

(56) References Cited

U.S. PATENT DOCUMENTS

| | | | | |
|---|---|---|---|---|
| 10,149,958 | B1 * | 12/2018 | Tran | G16H 50/20 |
| 10,216,762 | B2 * | 2/2019 | Kozuka | G06F 16/5838 |
| 10,657,838 | B2 * | 5/2020 | Garnavi | G16H 50/20 |
| 11,100,606 | B1 * | 8/2021 | Dickie | G16H 30/40 |
| 11,380,432 | B2 * | 7/2022 | Glottmann | G06T 7/0012 |
| 11,457,871 | B2 * | 10/2022 | Lyman | G06T 7/0002 |
| 11,553,874 | B2 * | 1/2023 | Hillen | G06F 18/2413 |
| 11,571,183 | B2 * | 2/2023 | Lee | A61B 8/565 |
| 11,847,798 | B2 * | 12/2023 | Lu | A61B 5/0077 |
| 12,087,431 | B2 * | 9/2024 | Urness | G16H 40/67 |
| 2007/0061393 | A1 | 3/2007 | Moore | |
| 2017/0061286 | A1 * | 3/2017 | Kumar | G06Q 30/0269 |
| 2017/0076046 | A1 | 3/2017 | Barnes | |
| 2017/0124258 | A1 | 5/2017 | Fritsch | |
| 2018/0341833 | A1 | 11/2018 | Bernard | |
| 2019/0005199 | A1 | 1/2019 | Rowley | |
| 2021/0158946 | A1 | 5/2021 | Starobinets | |
| 2022/0005187 | A1 * | 1/2022 | Lyman | G16H 40/20 |
| 2022/0051771 | A1 * | 2/2022 | Lyman | G06T 7/0014 |
| 2022/0068449 | A1 * | 3/2022 | Klassen | G16H 15/00 |
| 2023/0017291 | A1 * | 1/2023 | Raghavan | A61B 8/4245 |
| 2023/0146840 | A1 * | 5/2023 | Baldauf-Lenschen | G16H 10/20 703/11 |
| 2026/0038678 | A1 * | 2/2026 | Chaduvula | G16H 30/40 |

OTHER PUBLICATIONS

Jonnathan Coleman: Healthcare Turnover Rates; Jun. 20, 2023 https://www.dailypay.com/blog/employee-turnover-rates-in-the-healthcare-industry/.

* cited by examiner 100
102
Obtain exam data
104
Remove PII from data
106
Generate training materials from data
108
Tag training materials with tags
110
Select and display training materials during exam
111
Select and display training materials for review prior to performing an exam
112
Suggest scan parameter for exam

METHOD AND SYSTEM FOR DATA ACQUISITION PARAMETER RECOMMENDATION AND TECHNOLOGIST TRAINING

CROSS REFERENCE TO RELATED APPLICATIONS

This application is the U.S. National Phase application under 35 U.S.C. § 371 of International Application No. PCT/EP2022/075280 filed Sep. 12, 2022, which claims the benefit of U.S. Provisional Patent Application No. 63/247,380 filed Sep. 23, 2021. These applications are hereby incorporated by reference herein.

The following relates generally to the imaging arts, remote imaging assistance arts, remote imaging examination monitoring arts, technology assessment arts, technologist development arts, and related arts.

BACKGROUND

Radiology operations command centers (ROCCs) provide infrastructure for large imaging centers or integrated delivery networks (IDNs) with pools of technologist ("tech") talent to share tech expertise across an entire imaging network. By providing a communication channel (e.g., telephonic, videoconferencing, or so forth) and remote imaging device controller console sharing, an ROCC empowers the more experienced techs to provide guidance and oversight for junior techs when working with an imaging modality or workflow they may not be familiar or comfortable with.

For medical imaging, data acquisition parameters are set and adjusted by the technologist. Some parameters, such as field-of-view, need to be set during data acquisition. Improper imaging parameters may lead to low quality of the acquired images which in turn lead to errors in diagnosis. Setting and adjusting the parameters can be time-consuming and prone to errors, especially for inexperienced technologists. Current software on imaging scanners provides limited support for parameter setting and typically only the ranges of valid parameters are given, without task-specific optimization, which can result in issues for inexperienced technologists. There can be challenges when timely guidance for inexperienced technologists on parameter setting is needed.

The following discloses certain improvements to overcome these problems and others.

SUMMARY

In one aspect, a non-transitory computer readable medium stores instructions executable by at least one electronic processor to perform an operator assistance method including: obtaining data related to reference imaging examinations during performance of the medical imaging examinations; generating training materials from the obtained data; the training materials being related to the performance of the reference medical imaging examinations; and providing training user interface (UI) on a display device, the training UI displaying a visualization of a selected portion of the training materials which is selected based on information about a current or upcoming medical imaging examination.

In another aspect, a non-transitory computer readable medium stores instructions executable by at least one electronic processor to perform an operator assistance method including: retrieving training materials from a training database, the training materials including one or more tags corresponding to parameters of the medical imaging examination; analyzing the training materials to identify one or more suggested scan parameters for a current or upcoming medical imaging examination; and providing an operator assistance UI on a display device operable by an operator performing or scheduled to perform the current or upcoming medical imaging examination, the operator assistance UI displaying the one or more suggested scan parameters.

One advantage resides in creating a repository of de-identified (e.g., with sensitive patent information removed) video recordings scraped from console screens during scan acquisitions, with a sophisticated video tagging approach and robust recommendation algorithms matching technologists to appropriate training materials.

Another advantage resides in providing imaging training materials for technologists to prepare for the imaging scans or be accessed during the scan to ensure proper image acquisition.

Another advantage resides in reducing training time for new technologists.

Another advantage resides in quickly training new technologists to perform imaging scans.

Another advantage resides in retrieving imaging parameter used in similar imaging scans from a database and using the parameters to provide recommendations for parameter settings of a current imaging scan.

Another advantage resides in providing recommendations for imaging scan parameter settings for a junior technologist when a senior technologist is unavailable to assist the junior technologist.

Another advantage resides in tagging imaging parameters from previous imaging scans and using the tagged parameters for a current imaging scan.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
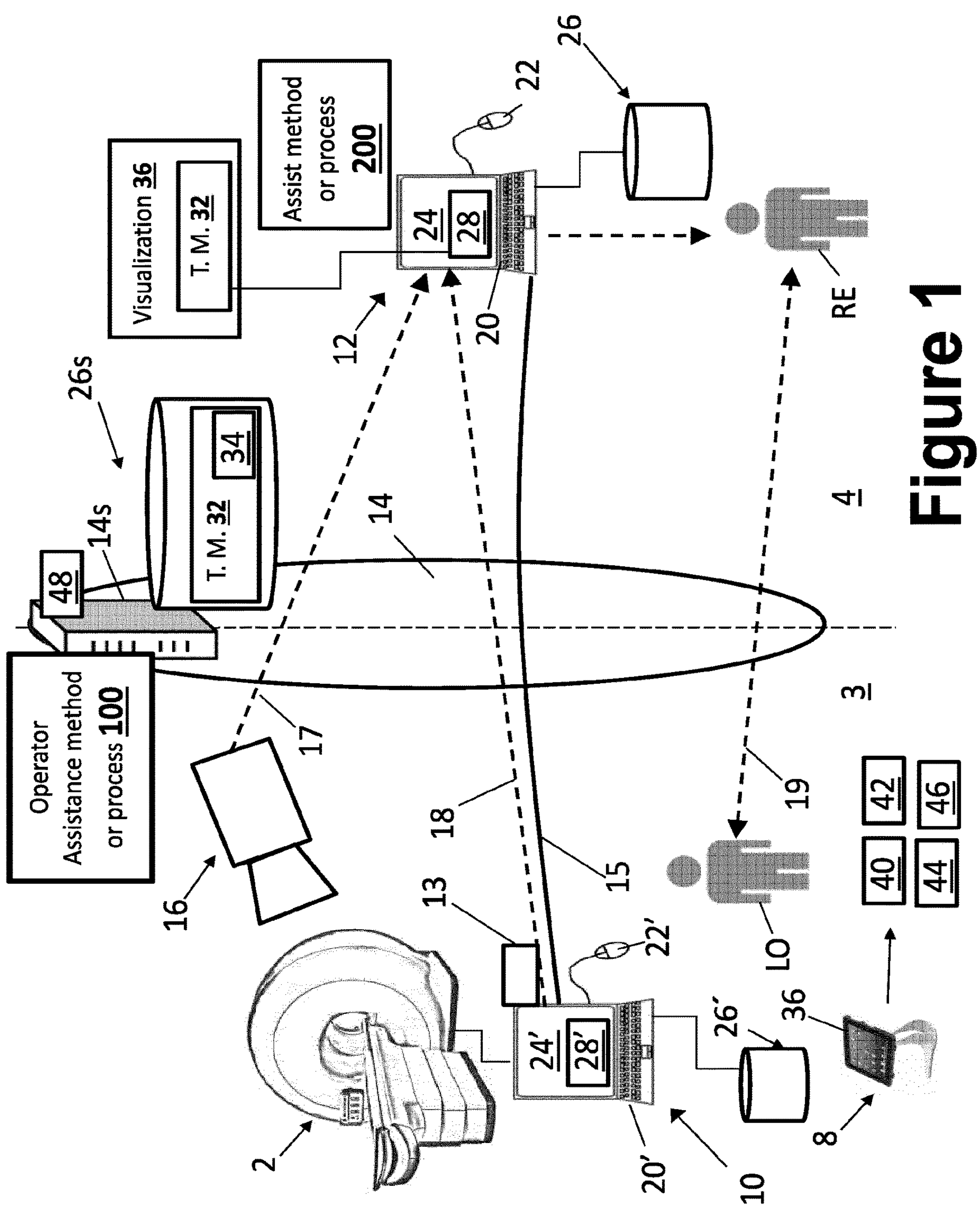
FIG. 1 diagrammatically shows an illustrative apparatus for providing remote assistance in accordance with the present disclosure.

Disclosed herein are systems and methods for providing task-specific recommendations on data acquisition parameters in real-time, based on parameters used in similar data acquisitions from a database. The method improves the adherence to imaging protocols, accelerates the data acquisition, and reduces errors due to inappropriate setting of imaging parameters.

Moreover, on collaboration platforms that enable virtualized imaging operations, virtual scanner access (ability for expert users located remotely to view and access scanner console screens from afar) can be used to support training. Video recordings of scanning sessions is one of the by-products of virtualized imaging. These video recordings can be used 1) to create an IDN-specific training platform for junior technologists and 2) to support quality imaging for technologists at all levels of experience. In effect, a training and assistive system supports provide medical image technologists with real-world example instructional videos on operating scanners as well as provide the technologists with task specific imaging parameters for the scanners while in operation.

The following relates to systems and methods that provide remote expert or "supertech" assistance to a local technician performing an imaging examination, such as a Radiology Operations Command Center (ROCC) system. A ROCC collects information on the imaging examination being performed by the local technician, which is supplied to the supertech to enable the supertech to provide effective assistance. The provided information typically includes, for example, a copy of the imaging device controller display. It is recognized herein that this collected information can be leveraged for other purposes.

ROCCs can serve as a training platform where junior technologists can take advantage of a database of video recordings captured during the actual acquisitions. Most radiologic technologists complete postsecondary programs in radiology that include theoretical study in the classroom and practical on-site clinical training. However, due to the sheer volume of imaging protocols, vendor-specific acquisition details and hospital-specific practices, technologists go through a significant amount of "on the job" coaching and training. This usually involves a senior or a lead technologist supervising junior tech's cases for up to 3-6 months and the need for assistance in special or complex cases for a significant time period thereafter. Typically, there are no IDN-specific training materials that could be used to bridge the new hire gap, speed up the training process, and free senior technologist's time. Institutions with high staff turn-over rates feel the pain of technologist training keenly. In some embodiments disclosed herein, ROCCs can accelerate and automate technologist training processes using IDN-specific materials.

Moreover, for medical imaging, the data acquisition parameters are set and adjusted by the technologist according to an imaging protocol. Setting and adjusting the parameters can be time-consuming and prone to errors, especially for inexperienced technologist. Improper imaging parameters may lead to low quality of the acquired images which in turn leads to errors in diagnosis or cause rescans to be performed. Current software on the scanner provides limited support for parameter value selection. Typically, only the valid value ranges of parameters are given, without optimization for specific task or protocol. The imaging protocol recommended for a study specifies a field-of-view (FOV) for a good quality study. This provides coverage of specific anatomical extent (e.g., apices to adrenals for a chest CT), with additional attributes like breath hold/inspiration etc. However, it is up to the technologist to set the FOV manually based on the images acquired in a navigator/scout scan.

Although support from an expert user is available through the ROCC, depending on the availability of remote expert user, waiting on an expert to provide real-time assistance via the ROCC can introduce undesirable delays in the imaging workflow.

The quality of images acquired with ROCC assistance, and the success achieved by use of an ROCC depends in part on how well the needs of the local techs are anticipated. However, assessing the knowledge and skills of individuals and evaluating their ability to perform the required tasks is difficult to do.

In some embodiments disclosed herein, controller screen videos scraped by the ROCC and (if available) scanner room videos from the ROCC can be mined to generate training material, and provide an efficient user interface to push such material to a technologist, either prior to an examination or in "real-time" during an examination.

The ROCC already records the scraped controller screen and (in some embodiments) scanner room videos in due course of providing expert assistance via the ROCC. In some embodiments herein, this recordation may be extended beyond those time intervals when expert assistance is being provided, in order to generate training materials. To enable these to be used as training materials, they are de-identified by removing personally identifying information and any irrelevant patient health-related information. The resulting de-identified videos are semantically tagged. This may leverage information automatically generated during the ROCC assistance procedure. For example, the ROCC system analyzes scraped console display frames to determine information such as vendor, scan type, workflow stage, and so forth. The video is preferably segmented so that individual segments of video may be tagged with the depicted workflow stage. Additionally, in some embodiments the technologist who performed the recorded examination (or alternatively an expert) may add tags to the video segments. The tagged video is collected in a training database.

The disclosed system further provides mechanisms for pushing the training video to technologists. This can be done ahead of time based on matching scheduled examination parameters with tags of the videos. For example, the technologist may receive an email, text message, or other alert providing recommended videos that can be viewed via a website or mobile device app. Additionally, access to videos may be provided in real-time to the technologist during an imaging examination. For example, if the technologist runs into a difficulty, he or she can open the ROCC app on a tablet or cellphone and type in a search query which (optionally along with information extracted by the ROCC system for the technologist's current examination) retrieves relevant video(s) for the technologist to review. In the case of providing assistance in real-time during a current examination, in some contemplated embodiments the ROCC app may optionally utilize Bluetooth™, Wi-Fi, or another wireless communication protocol supported by the ROCC tablet or cellphone to read information about the state of the current examination directly from the imaging device controller, if the controller supports such wireless connectivity for data transfer. In this case, the user interface can be greatly simplified, e.g., the technician can simply select a menu option labeled "Assistance with current exam" or similar nomenclature in the app to trigger the search based on the information wirelessly received from the imaging device controller. The tags can provide quicker guidance to the specific portion of the current exam that requires assistance.

The ROCC website and/or mobile app preferably provides the technologist with various options for expediting the review of the training video content. For example, the video player can include accelerated playback options, segment-skip, and so forth.

In other embodiments disclosed herein, the tagged database content can be used to identify scan parameters for suggestion to a technologist performing a current examination. Scan parameters may be extracted from scraped scanner console video frames as part of the ROCC assistance process, or specially extracted for the parameter recommender. This creates a database of examination (characterized by various tags, e.g., modality, scan type, et cetera) and corresponding imaging parameters.

In some examples, a similarity-experience level metric is computed for each examination in the database, which is a product of (i) a similarity metric measuring similarity of the current examination to the archive video and (ii) an experience level of the technologist who performed the examination of the archive video. Since a given imaging parameter may have different values in different "close" database examinations, in one embodiment a graphical representation is provided to the user via the mobile app, plotting the different imaging parameter values along a horizontal line color-coded by the similarity-experience score. By clicking on a datapoint more information about the examination is brought up. In a possible tie-in option, selecting a datapoint might bring up the training video for that examination.

In particular examples, the field-of-view (FOV) imaging parameter is analyzed. In this example, the technologist acquires scout scans of the patient which are fed into a CNN to detect most similar scout scans in the database. The scout scans of the N closest exams are spatially registered with the scout scan of the current examination, and that transformation is used to transform the FOV corner points of the closest exams to the frame-of-reference of the current scan in order to provide recommended FOV values.

With reference to FIG. 1, an apparatus for providing assistance from a remote medical imaging expert RE (or supertech) to a local technician operator LO is shown. Such a system is also referred to herein as a radiology operations command center (ROCC). As shown in FIG. 1, the local operator LO, who operates a medical imaging device (also referred to as an image acquisition device, imaging device, and so forth) 2, is located in a medical imaging device bay 3, and the remote expert RE is disposed in a remote service location or center 4. It should be noted that the remote expert RE may not necessarily directly operate the medical imaging device 2, but rather provides assistance to the local operator LO in the form of advice, guidance, instructions, or the like. The remote location 4 can be a remote service center, a radiologist's office, a radiology department, and so forth. The remote location 4 may be in the same building as the medical imaging device bay 3 (this may, for example, in the case of a remote expert RE who is a radiologist tasked with peri-examination image review), or the remote service center 4 and the medical imaging device bay 3 may be in different buildings, and indeed may be located in different cities, different countries, and/or different continents. In general, the remote location 4 is remote from the imaging device bay 3 in the sense that the remote expert RE cannot directly visually observe the imaging device 2 in the imaging device bay 3 (hence optionally providing a video feed as described further herein).

The image acquisition device 2 can be a Magnetic Resonance (MR) image acquisition device, a Computed Tomography (CT) image acquisition device; a positron emission tomography (PET) image acquisition device; a single photon emission computed tomography (SPECT) image acquisition device; an X-ray image acquisition device; an ultrasound (US) image acquisition device; or a medical imaging device of another modality. The imaging device 2 may also be a hybrid imaging device such as a PET/CT or SPECT/CT imaging system. While a single image acquisition device 2 is shown by way of illustration in FIG. 1, more typically a medical imaging laboratory will have multiple image acquisition devices, which may be of the same and/or different imaging modalities. For example, if a hospital performs many CT imaging examinations and relatively fewer MRI examinations and still fewer PET examinations, then the hospital's imaging laboratory (sometimes called the "radiology lab" or some other similar nomenclature) may have three CT scanners, two MRI scanners, and only a single PET scanner. This is merely an example. Moreover, the remote service center 4 may provide service to multiple hospitals. The local operator LO controls the medical imaging device 2 via an imaging device controller 10. The remote expert RE is stationed at a remote workstation 12 (or, more generally, an electronic controller 12).

As used herein, the term "medical imaging device bay" (and variants thereof) refer to a room containing the medical imaging device 2 and also any adjacent control room containing the medical imaging device controller 10 for controlling the medical imaging device. For example, in reference to an MRI device, the medical imaging device bay 3 can include the radiofrequency (RF) shielded room containing the MRI device 2, as well as an adjacent control room housing the medical imaging device controller 10, as understood in the art of MRI devices and procedures. On the other hand, for other imaging modalities such as CT, the imaging device controller 10 may be located in the same room as the imaging device 2, so that there is no adjacent control room and the medical bay 3 is only the room containing the medical imaging device 2. The imaging device controller 10 includes an electronic processor 20', at least one user input device such as a mouse 22', a keyboard, and/or so forth, and a display device 24'. The imaging device controller 10 presents a device controller graphical user interface (GUI) 28' on the display 24' of the imaging device controller 10, via which the local operator LO accesses device controller GUI screens for entering the imaging examination information such as the name of the local operator LO, the name of the patient and other relevant patient information (e.g. gender, age, etc.) and for controlling the (typically robotic) patient support to load the patient into the bore or imaging examination region of the imaging device 2, selecting and configuring the imaging sequence(s) to be performed, acquiring preview scans to verify positioning of the patient, executing the selected and configured imaging sequences to acquire clinical images, display the acquired clinical images for review, and ultimately store the final clinical images to a Picture Archiving and Communication System (PACS) or other imaging examinations database. In addition, while FIG. 1 shows a single medical imaging device bay 3, it will be appreciated that the remote service center 4 (and more particularly the remote workstation 12) is in communication with multiple medical bays via a communication link 14, which typically comprises the Internet augmented by local area networks at the remote operator RE and local operator LO ends for electronic data communications.

As diagrammatically shown in FIG. 1, in some embodiments, a camera 16 (e.g., a video camera) is arranged to acquire a video stream 17 of a portion of the medical imaging device bay 3 that includes at least the area of the imaging device 2 where the local operator LO interacts with the patient, and optionally may further include the imaging device controller 10. The video stream 17 is sent to the remote workstation 12 via the communication link 14, e.g., as a streaming video feed received via a secure Internet link.

In some examples, as shown in FIG. 1, the camera 16 can be affixed to a wall of ceiling of the medical facility with a field of view to include the area of the imaging device 2 where the local operator LO interacts with the patient, and optionally may further include the imaging device controller 10. In other examples, the camera 16 can be disposed within an imaging bore (not shown) of the imaging device 2.

In other embodiments, the live video feed 17 of the display 24' of the imaging device controller 10 is, in the illustrative embodiment, provided by a video cable splitter 15 (e.g., a DVI splitter, a HDMI splitter, and so forth). In other embodiments, the live video feed 17 may be provided by a video cable connecting an auxiliary video output (e.g. aux vid out) port of the imaging device controller 10 to the remote workstation 12 of the operated by the remote expert RE. Alternatively, a screen mirroring data stream 18 is generated by screen sharing software 13 running on the imaging device controller 10 which captures a real-time copy of the display 24' of the imaging device controller 10, and this copy is sent from the imaging device controller 10 to the remote workstation 12. Other approaches besides the illustrative video cable splitter 15 or screen sharing software 13 are contemplated for capturing a real-time copy of the display 24' of the imaging device controller 10 which is then sent to the workstation 12 of the remote expert RE. While in an ROCC this real-time copy of the display 24' of the imaging device controller 10 is used to provide status information to the remote expert RE for use in assisting the local operator LO, in embodiments disclosed herein the real-time copy of the display 24' of the imaging device controller 10 is also leveraged (optionally along with other available information) to determine one or more performance metrics of the local operator LO.

The communication link 14 also provides a natural language communication pathway 19 for verbal and/or textual communication between the local operator LO and the remote expert RE, in order to enable the latter to assist the former in performing the imaging examination. For example, the natural language communication link 19 may be a Voice-Over-Internet-Protocol (VOIP) telephonic connection, a videoconferencing service, an online video chat link, a computerized instant messaging service, or so forth. Alternatively, the natural language communication pathway 19 may be provided by a dedicated communication link that is separate from the communication link 14 providing the data communications 17, 18, e.g., the natural language communication pathway 19 may be provided via a landline telephone. In another example, the natural language communication pathway 19 may be provided via an ROCC device 8, such as a mobile device (e.g., a tablet computer or a smartphone). For example, an "app" can run on the ROCC device 8 (operable by the local operator LO) and the remote workstation 12 (operable by the remote expert RE) to allow communication (e.g., audio chats, video chats, and so forth) between the local operator and the remote expert.

FIG. 1 also shows, in the remote service center 4 including the remote workstation 12, such as an electronic processing device, a workstation computer, or more generally a computer, which is operatively connected to receive and present the video 17 of the medical imaging device bay 3 from the camera 16 and to present the screen mirroring data stream 18 as a mirrored screen. Additionally or alternatively, the remote workstation 12 can be embodied as a server computer or a plurality of server computers, e.g., interconnected to form a server cluster, cloud computing resource, or so forth. The workstation 12 includes typical components, such as an electronic processor 20 (e.g., a microprocessor), at least one user input device (e.g., a mouse, a keyboard, a trackball, and/or the like) 22, and at least one display device 24 (e.g., an LCD display, plasma display, cathode ray tube display, and/or so forth). In some embodiments, the display device 24 can be a separate component from the workstation 12. The display device 24 may also comprise two or more display devices, e.g., one display presenting the video 17 and the other display presenting the shared screen (i.e., display 24') of the imaging device controller 10 generated from the screen mirroring data stream 18. Alternatively, the video and the shared screen may be presented on a single display in respective windows. The electronic processor 20 is operatively connected with a one or more non-transitory storage media 26. The non-transitory storage media 26 may, by way of non-limiting illustrative example, include one or more of a magnetic disk, RAID, or other magnetic storage medium; a solid-state drive, flash drive, electronically erasable read-only memory (EEROM) or other electronic memory; an optical disk or other optical storage; various combinations thereof; or so forth; and may be for example a network storage, an internal hard drive of the workstation 12, various combinations thereof, or so forth. It is to be understood that any reference to a non-transitory medium or media 26 herein is to be broadly construed as encompassing a single medium or multiple media of the same or different types. Likewise, the electronic processor 20 may be embodied as a single electronic processor or as two or more electronic processors. The non-transitory storage media 26 stores instructions executable by the at least one electronic processor 20. The instructions include instructions to generate a graphical user interface (GUI) 28 for display on the remote operator display device 24.

The medical imaging device controller 10 in the medical imaging device bay 3 also includes similar components as the remote workstation 12 disposed in the remote service center 4. Except as otherwise indicated herein, features of the medical imaging device controller 10 disposed in the medical imaging device bay 3 similar to those of the remote workstation 12 disposed in the remote service center 4 have a common reference number followed by a "prime" symbol (e.g., processor 20', display 24', GUI 28') as already described. In particular, the medical imaging device controller 10 is configured to display the imaging device controller GUI 28' on a display device or controller display 24' that presents information pertaining to the control of the medical imaging device 2 as already described, such as imaging acquisition monitoring information, presentation of acquired medical images, and so forth. It will be appreciated that the real-time copy of the display 24' of the controller 10 provided by the video cable splitter 15 or the screen mirroring data stream 18 carries the content presented on the display device 24' of the medical imaging device controller 10. The communication link 14 allows for screen sharing from the display device 24' in the medical imaging device bay 3 to the display device 24 in the remote service center 4. The GUI 28' includes one or more dialog screens, including, for example, an examination/scan selection dialog screen, a scan settings dialog screen, an acquisition monitoring dialog screen, among others. The GUI 28' can be included in the video feed 17 or provided by the video cable splitter 15 or by the mirroring data stream 17' and displayed on the remote workstation display 24 at the remote location 4.

FIG. 1 shows an illustrative local operator LO, and an illustrative remote expert RE (i.e., expert, e.g., supertech). However, the ROCC optionally provides a staff of supertechs who are available to assist local operators LO at different hospitals, radiology labs, or the like. The ROCC may be housed in a single physical location or may be geographically distributed. For example, in one contemplated implementation, the remote operators RO are recruited from across the United States and/or internationally in order to provide a staff of supertechs with a wide range of expertise in various imaging modalities and in various imaging procedures targeting various imaged anatomies. In view of this multiplicity of local operators LO and multiplicity of remote operators RO, the disclosed communication link 14 includes a server computer 14*s* (or a cluster of servers, cloud computing resource comprising servers, or so forth) which is programmed to establish connections between selected local operator LO/remote expert RE pairs. For example, if the server computer 14*s* is Internet-based, then connecting a specific selected local operator LO/remote expert RE pair can be done using Internet Protocol (IP) addresses of the various components 16, 10, 12, the telephonic or video terminals of the natural language communication pathway 19, et cetera. The server computer 14*s* is operatively connected with a one or more non-transitory storage media 26*s*. The non-transitory storage media 26*s* may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the server computer 14*s*, various combinations thereof, or so forth. It is to be understood that any reference to a non-transitory medium or media 26*s* herein is to be broadly construed as encompassing a single medium or multiple media of the same or different types. Likewise, the server computer 14*s* may be embodied as a single electronic processor or as two or more electronic processors. The non-transitory storage media 26*s* stores instructions executable by the server computer 14*s*. In addition, the non-transitory computer readable medium 26*s* (or another database) stores data related to a set of remote experts RE and/or a set of local operators LO. The remote expert data can include, for example, skill set data, work experience data, data related to ability to work on multi-vendor modalities, data related to experience with the local operator LO and so forth.

Furthermore, as disclosed herein the server 14*s* performs an operator assistance method or process 100 for assisting a local medical imaging device operator LO during imaging examinations performed using one or more of the medical imaging devices 2. The assessment method 100 advantageously leverages information sources provided by the ROCC, such as the content of the display 24' of the imaging device controller display.

The server computer 14*s* can also store data related to relevant information acquired during each imaging examination performed by a local operator LO. The stored data can include, for example, a vendor and modality of the medical imaging device 2 used in the imaging examination, an identification of the local medical imaging device operator LO, a modality of the medical imaging device an identification of the medical imaging device, an assigned current procedural terminology code, an identification of whether assistance from a remote medical expert was used, communication notes between the local operator and the remote medical expert, patient data (e.g., frail individuals, pediatric exams, disabled individuals, and so forth), a duration of the imaging examination, sequences repeated during the imaging examination, quality of images acquired during the imaging examination, notes regarding adversary events (e.g., device malfunction), and so forth.

Figure 2:
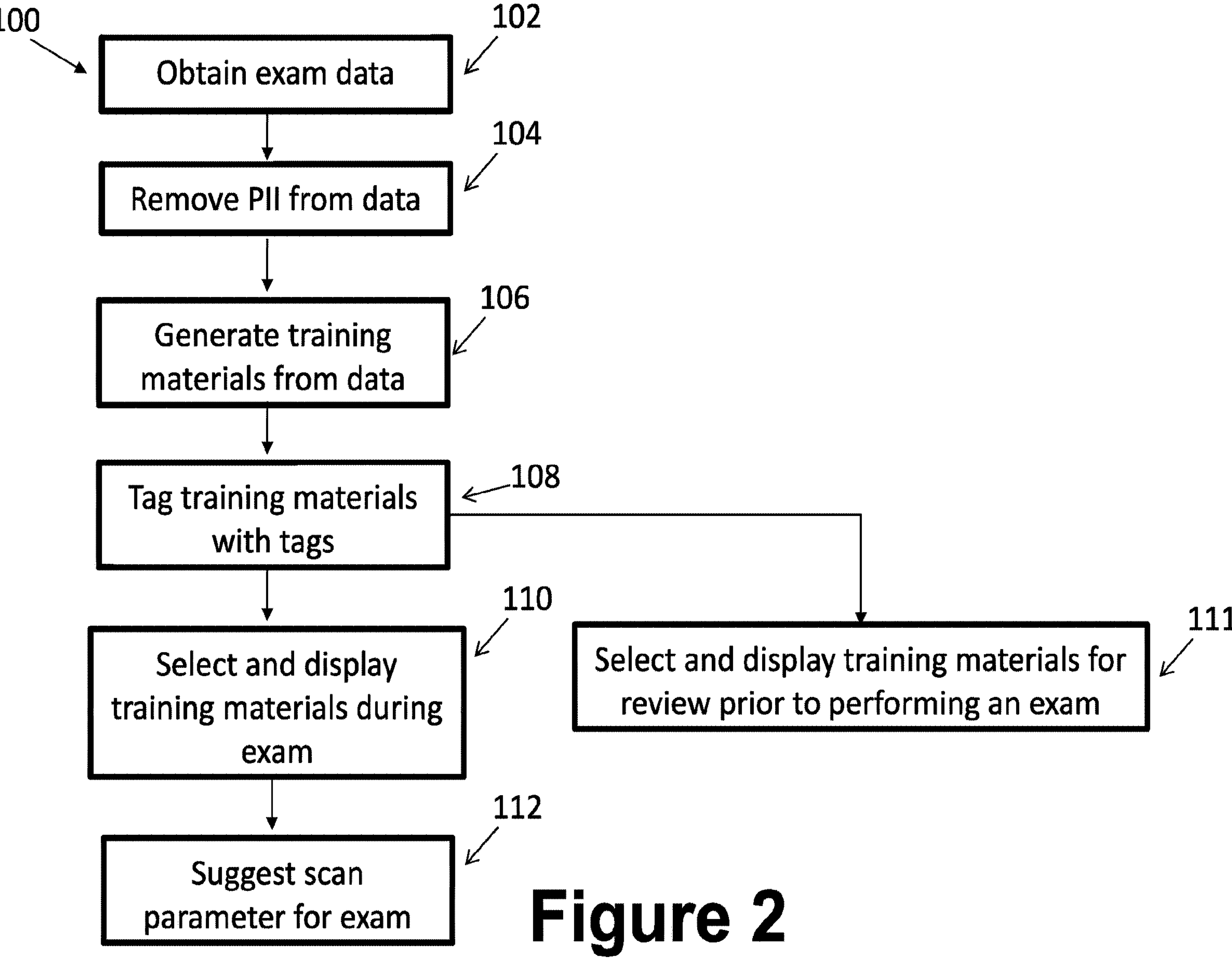
FIGS. 2 and 3 show example flow charts of operations suitably performed by the apparatus of FIG. 1.

With reference to FIG. 2, and with continuing reference to FIG. 1, an illustrative embodiment of the operator assistance method 100 is diagrammatically shown as a flowchart. The first operations 102, 104, 106, 108 relate to the creation of the training materials. These operations 102, 104, 106, 108 may be performed for all imaging examinations, or for some subset, e.g., for imaging examinations performed by more senior and skilled imaging technicians so that the subsequently extracted training materials reflect a high level of expertise. The subsequent operations 110, 111, 112 relate to the consumption of the created training materials. These operations 110, 111, 112 are typically performed in conjunction with a more junior and possibly less skilled imaging technician, and are intended to assist the technician by providing training and/or automatically recommending values for scan parameters. However, even highly skilled, and experienced imaging technicians may choose to utilize the available training materials as described herein with reference to operations 110, 111, 112.

The training materials are generated as follows. At an operation 102, data related to reference imaging examinations is obtained during performance of the medical imaging examinations. The obtaining operation 102 includes screen-scraping data displayed on the display device 24' of the medical imaging device controller 10 of the medical imaging device 2. This screen-scraping leverages the availability of the real-time copy of the display 24' of the imaging device controller 10 provided by the ROCC system, for example using the video cable splitter 15 or the screen sharing software 13. The screen scraping can use any suitable approach for extracting relevant information from the real-time copy of the display 24' of the imaging device controller 10. For example, video frames can be analyzed by optical character recognition (OCR) to extract text. As the imaging device controller GUI 28' typically uses standardized dialog screens, the screen scraping can leverage a priori knowledge about the layouts of these dialog screens to enable more precise information extraction. For example, if a dialog screen has one input area for entry of the local operator LO identification and another input area for entry of the patient identification, then this a priori knowledge of the layout can be used to distinguish the local operator and patient names. Similarly, specific dialog screens may be brought up for specific imaging sequences, and recognition of these specific dialog screens in the real-time copy of the display 24' of the imaging device controller 10 enables extraction of the selected imaging sequence, and a priori knowledge of the layouts of these dialog screens can be used to correlate numeric or other inputs to specific scan parameters. These are merely some non-limiting illustrative examples of information extraction approaches suitably used in the screen-scraping. The data displayed on the display device 24' of a medical imaging device controller 10 typically includes information useful to the technician assessment method 100 such as an identification of the local medical imaging device operator LO, a modality of the medical imaging device 2, an identification of the medical imaging device, an assigned current procedural terminology code, an identification of whether assistance from a remote medical expert was used, and patient data.

In another example, the obtaining operation 102 includes recording images of an imaging examination performed by the local operator LO with the camera 16, and recording audio or textual conversations between the local operator and the remote medical expert during the imaging examination via the natural language communication pathway 19. The data can then be obtained from the recorded images and recorded conversations. The obtained data can also be stored in the server computer 14*s*.

The foregoing examination data gathering operation 102 is suitably performed each time the local operator LO performs an imaging examination with the ROCC in operation. In some embodiments, the ROCC operation is modified to generate the real-time copy of the display 24' of the controller 10 provided by the video cable splitter 15 or the screen mirroring data stream 18 throughout each examination, even if the local operator LO does not utilize assistance of a remote expert via the ROCC. In this way, the existing hardware of the ROCC (e.g., the video cable splitter 15 or the screen mirroring software 13) is leveraged to ensure that examination data collection occurs for all examinations, regardless of whether and for how long the ROCC is utilized. The examination data collected over days, weeks, months, or longer are suitably collected to provide a sizable database of examination data for the local operator LO that may include many dozens, hundreds, or more imaging examinations performed by the local operator LO. In other embodiments, the examination data gathering operation 102 may be performed only for certain imaging examinations, such as, by way of example, only for imaging examinations performed by designated senior operators who are expected to provide high quality examples, or only for imaging examinations which the performing operator affirmatively chooses to have recorded.

The operations 104, 106, 108 then process the examination data collected at operation 102 to create a database of training materials. The operations 104, 106, 108 may be performed for all examination data collected in the operation 102, or for some subset of that information. For example, at the end of an examination the technician may be asked whether he or she authorizes the examination data to be used for creating training material. This would allow the technician to exclude imaging examinations the technician deems to be of lower quality. Additionally, since the extraction of training materials from the examination data of an imaging examination may entail input from the imaging technician (e.g., in some implementations of the tagging operation 108), the technician may elect not to authorize an examination to be included in the training materials to avoid providing this input, or a radiologist may review a particular examination result and indicate that it is a good candidate for training material creation. Training materials are extracted from the examination data collected at operation 102 as follows. At an operation 104, personally identifiable information (PII) can be removed from the obtained data. The PII that is removed can include personal health information (PHI) (e.g., name, medical record number, date of birth, date of image acquisition, and so forth). Since the disclosed ROCC system is a vendor-agnostic, multi-modal, backwards compatible platform, video anonymization algorithms can automatically identify and remove PHI information for recordings acquired on different modalities of different medical imaging devices 2 manufactured by different vendors. When relevant, console recordings can be supplemented by anonymized scanner room videos demonstrating proper patient positioning, proper set up of auxiliary equipment (i.e., gating belts), etc. To anonymize the obtained data, a machine learning algorithm can be implemented searching video frames for PHI information and either removing or replacing patient-sensitive information with fake data. The algorithm can support anonymization for videos acquired in a multi-modality, multi-vendor way. Additionally, face detection and anonymization can be performed for in-scanner room videos.

At an operation 106, training materials 32 (e.g., videos, documents, presentations, etc.) are generated from the processed data output from the operation 104. In the operation 106, only video fragments covering relevant imaging workflow elements can be retained for training purposes such as patient positioning within a scanner, coil placement, patient coaching, room clean-up, etc. Various approaches can be used to discard other examination data that may not be useful for the training. For example, if the scraped controller display does not change for several minutes because the operator is not interacting with the controller, then this time duration of scraped controller display can be shortened by retaining only a subset of the scraped controller screen frames. The operation 106 may also include processing of the examination data that is retained as the training materials 32 to make it more useful. For example, in video of the scraped controller screen, elements that change (for example, corresponding to the user inputting a value, or to an acquired image appearing being displayed) can be highlighted by a bounding red box, by boldfacing added text, or by some other type of highlighting. In examination room video (or from sounds in the examination room video), the frames may be cropped and zoomed to better present relevant events. These are merely illustrative examples. The training materials 32 are related to the performance of the reference medical imaging examinations. The training materials 32 can be stored in the non-transitory computer readable medium 26*s* of the server computer 14*s*.

At an operation 108, the training materials 32 are tagged with one or more tags 34 generated from the obtained data. The tags 34 include, for respective reference medical imaging examinations, one or more of an identification of a medical imaging device operator who performed the reference medical imaging examination, a modality of the medical imaging device 2 used in performing the reference medical imaging examination, an identification of the medical imaging device used in performing the reference medical imaging examination, an assigned current procedural terminology code for the reference medical imaging examination, an identification of whether assistance from a remote medical expert was used during the reference medical imaging examination, and patient data of a patient examined by the reference medical imaging examination. Other types of tags 34 or annotations may be added as well, such as comments on what is going on during the examination annotated by the imaging technician who performed the imaging examination, temporal tags, and tags indicating which parameter is adjusted during a particular segment of the video stream. The training materials 32, tagged with the tags 34, can be stored in the non-transitory computer readable medium 26*s* of the server computer 14*s*.

The tagging 108 may be fully automated, or semi-automated. Imaging data associated with acquisition errors, artefacts, image quality issues can be tagged in an automatic manner (by reviewing radiology reports, running image quality algorithms, etc.), semi-automatic (reviewing radiology reports, image quality and prompting user action) or manual way (allowing user to supply additional tag). Furthermore, a tag 34 representing the difficulty level of the imaging examination can be created in an automatic (e.g., by using a machine learning model trained on a subset of videos with manually created tags) or manual manner. This makes it more convenient for preparing training materials for junior technologists, based on the difficulty level of the scans. Tags 34 for the video with one of the frames shown below may include, for example, CT, Abdomen I.D., Helical, Adult, Reduced Tube Voltage, extended FOV, etc. Manual tagging (if done at all) may be done by the imaging technician who performed the imaging examination immediately after completion of the examination. Additionally or alternatively, manual tagging may be done at some later time, either by the imaging technician who performed the examination or by some other qualified person (e.g., a senior imaging technician or radiologist).

In some embodiments, the obtained data comprises a video stream of the medical imaging examination, then the video stream can be segmented into a plurality of video stream segments, and each video stream segment can be tagged with one or more tags 34. In some examples, the segmenting of the video stream is based on at least one of a parameter change, sound change, or new step in the imaging protocol.

In some embodiments, to tag the training materials 32 with the tags 34, a training materials annotation UI 42 is provided on the display 36 of the ROCC device 8, by which a local operator who performed one of the reference medical imaging examinations tags the training materials 32 obtained during the reference medical imaging examination with the one or more tags 34. A selected portion of the training materials 32 can be selected by matching parameters of a current or upcoming medical imaging examination with the tags 34 of the training materials 32. A message indicating selected portion of the training materials to be reviewed based on the matching can be transmitted from the local operator who performed one of the reference medical imaging examinations to the local operator LO performing or scheduled to perform the current or upcoming medical imaging examination.

The tags 34 from the reference medical imaging examination can further include, for example, patient communication, safety and assistance, coil placement, contrast administration, contrast reaction monitoring, field-of-view selection, finding protocol parameters that are sometimes buried deep within menus, etc. These tags 34 enable the training materials 32 to become searchable by various tag entries.

The operations 102, 104, 106, 108 that create the training materials may be performed on an ongoing basis to keep the database of training materials up-to-date. Optionally, training materials may be phased out and removed from the database of training materials in an automated or semi-automated fashion. For example, if a particular make/model of imaging device is no longer in use by any radiology department that utilizes the training materials, then training data tagged with that make/model of imaging device may be phased out. Similarly, training material tagged with imaging procedure identifications that have become obsolete may be phased out. Optionally, manual curation of the training materials may also be performed. For example, a senior imaging technician or radiologist may periodically review the training materials and remove any training material that is deemed to be of low quality or otherwise not suitable.

With reference now to operations 110, 111, 112, a suitable approach for consumption of relevant training materials is next described.

At an operation 110, during a current imaging examination, a training UI 44 is provided either on the display 36 of the ROCC device 8, or alternatively on the GUI 28' on the display device 24' of the medical imaging device controller 10. The training UI 44 is configured to display a visualization 36 of a selected portion of the training materials 32 which is selected based on information about a current or upcoming medical imaging examination. In one example, the current or upcoming medical imaging examination is a current medical imaging examination, and the training materials 32 are provided to the local operator LO performing the current imaging examination during the current medical imaging examination. In another example, a radiologist may review a particular examination result and indicate that it is a good candidate for training material creation. In another example, the current or upcoming medical imaging examination is an upcoming medical imaging examination, and the training materials 32 are provided to the local operator LO prior to the upcoming medical imaging examination. In another example, when the local operator LO requires assistance, the natural language communication pathway 19 is established and used to allow the local operator LO and the remote operator RE to discuss the procedure and in particular to allow the remote operator to provide advice to the local operator LO. Additionally or alternatively, in an operation 111 training materials may be selected and displayed prior to an imaging examination, based for example on an upcoming schedule of imaging examinations to be performed by a given imaging technician.

To select relevant training materials 32 based on the tags 34, an algorithm can match a training video of the training materials 32 with a current or scheduled medical imaging examination. For example, if the local operator LO is performing, or is scheduled to perform, a cardiac imaging scan on, for example, a 3T Philips MRI scanner, then a video from a prior acquisition of a cardiac scan done on a 3T Philips MRI scanner retrieved from the training materials 32 and linked to the appointment in a scheduling system. The local operator LO may choose to view the suggested video content in preparation for the imaging examination. If the technician is currently performing the examination and realizes that assistance is needed, then the user can bring up an operator assistance UI 46 on the display device 36 of the ROCC device 8. In one approach, the user is provided with a search query entry dialog via which the user can enter relevant search terms specifying imaging modality (here MRI), scan type (here cardiac scan), and/or so forth, and the tags of the training materials are searched to identify and provide a list or other selection dialog via which the operator LO can select training material for retrieval and presentation. In a more advanced embodiment, if the ROCC device 8 is equipped with Bluetooth™, Wi-Fi, or another wireless communication protocol, then the imaging device controller 10 may optionally be programmed to interface with the assistance UI 40 to automatically provide information about the current imaging examination and the assistance UI 40 automatically constructs the search query from this automatically received information and retrieves and presents the search results to the operator LO. In either operation 110 or 111, additionally, some of the details from patient's medical record may be used to tailor the matching of training material. For instance, if the patient has a stent, then training material extracted from a previous imaging examination of a cardiac stented patient can be retrieved for the local operator LO to review. Alternative to the algorithmic search, the local operator LO may manually search through the training materials 32 using the tags 34. Local operators can watch selected videos (or other selected training material) retrieved from the training materials 32, which can be displayed on the ROCC device 8. In another example, when the natural language communication pathway 19 is established the local operator LO and the remote operator RE, the RE can select training materials to send or transmit to the local operator LO as part of an effort to reduce the time the RE is needed to reduce time spent with the local operator LO. For example, the LO initiates a remote connection to establish the natural language communication pathway 19. The local operator LO can explain the issue with the remote expert RE while the remote expert RE reviews the screen-scraped images of the medical imaging device bay 3, explains the trouble. The RE can determine any issues, and either gives quick response to fix or provides a suggested training. material(s) 32. If the suggested training material(s) 32 is used, the natural language communication pathway 19 can be reestablished with the RE if there are still questions or concerns from the local operator LO.

In the operation 111, in addition to the schedule of the local operator LO, past imaging examination records can be used to provide recommendations for training. The ROCC system can look for gaps in knowledge based on the imaging examination records performed by the local operator LO and is scheduled to perform, and make suggestions to supplement the record with training videos from the training materials 32. For example, if the local operator LO has not done an abdominal MRI on a Siemens scanner before; however, several abdominal scans are scheduled for the Siemens machine in the next few days or weeks, then the server computer 14*s* can calculate the likelihood that a particular local operator may be required to perform an unfamiliar exam and suggest a set of review/training videos from the training materials 32.

In some embodiments, the training materials 32 can be used to aid the local operator LO during the imaging examinations in real time. The local operator LO may be uncertain about the placement of, for example, a gating belt or an acquisition element (i.e., placement of fat suppression bands) and may choose to pull up a video recording to ensure the examination is being performed correctly. Closely matching a training video to the current exam (potentially even matching the stage of the scan) and providing a ready access to such materials would allow the local operator LO to quickly resolve any uncertainties. For example, for a medical imaging examination that has not yet started, a scanner room video depicting proper patient set-up might be most useful. In another example, for a medical imaging examination that is almost finished and requires image reformats, a video segment demonstrating proper image reformatting might be more appropriate. An algorithm can track progression of a live scan and if prompted provide a matched video of a prior exam, matched to the stage in the acquisition.

At an operation 112, at least one suggested scan parameter is determined for the current or upcoming medical imaging examination based on the generated training materials 32. The at least one suggested scan parameter can be displayed (e.g., on the ROCC device 8) to the local operator LO during or prior to the medical imaging examination.

Figure 3:
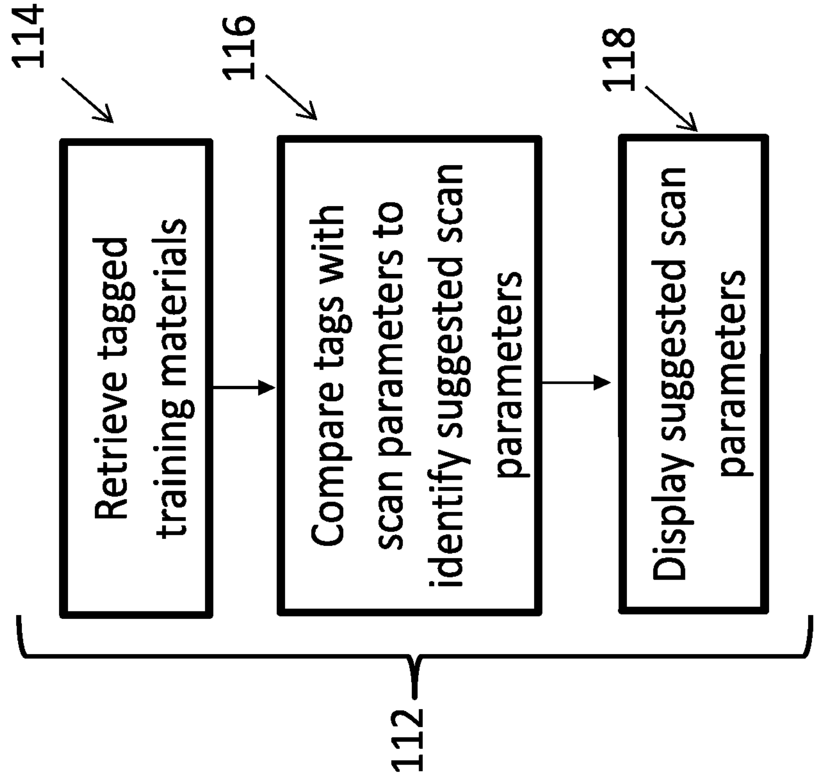

With reference to FIG. 3, and with continuing reference to FIGS. 1 and 2, an illustrative embodiment of the scan parameter recommendation operation 112 is diagrammatically shown as a flowchart. At an operation 114, the training materials 32, tagged with the tags 34, are then retrieved from the non-transitory computer readable medium 26*s* of the server computer 14*s*. At an operation 116, the training materials 32 are then analyzed to identify one or more suggested scan parameters for a current or upcoming medical imaging examination. To do so, the tags 34 of the training materials 32 are compared with scan parameters of the current medical imaging examination.

The comparing can include using a similarity-based metric for each medical imaging examination. The similarity-based metric can be determined by calculating a similarity metric measuring similarity of the current examination to the training materials 32. An experience level of the operator who performed the examination of the training materials is also determined, and the experience level is multiplied by the similarity metric.

Figure 4:
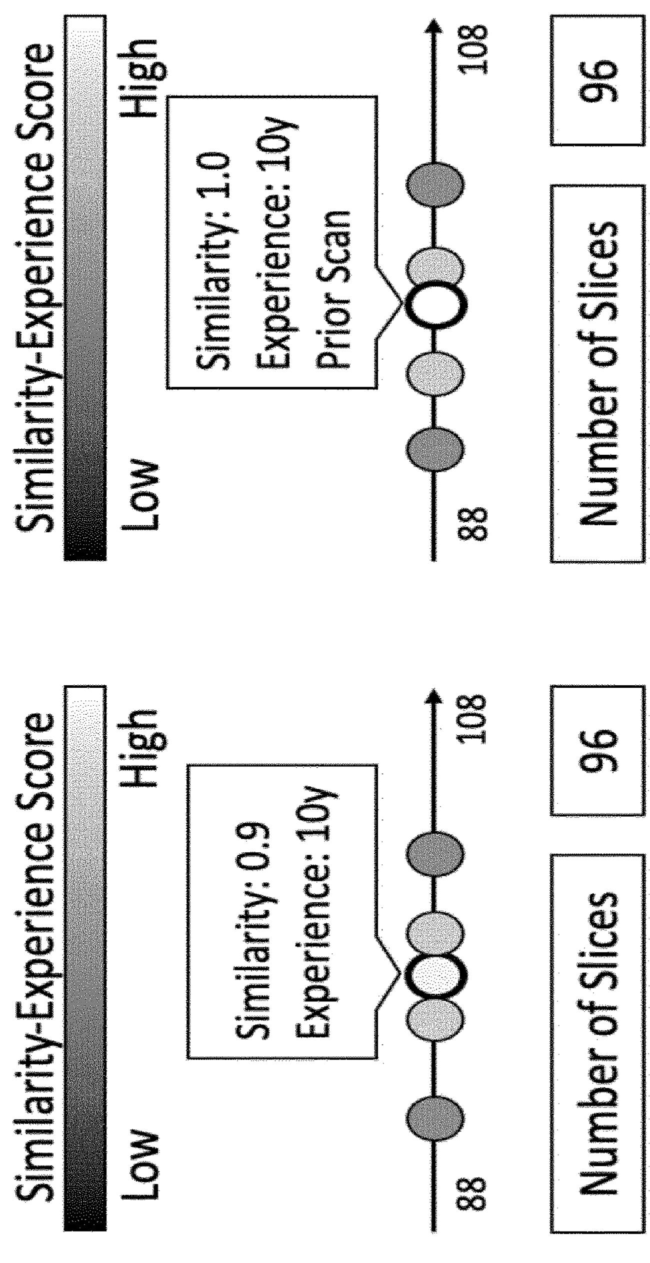
FIG. 4 shows an example of outputs generated by the apparatus of FIG. 1.
Figure 5:
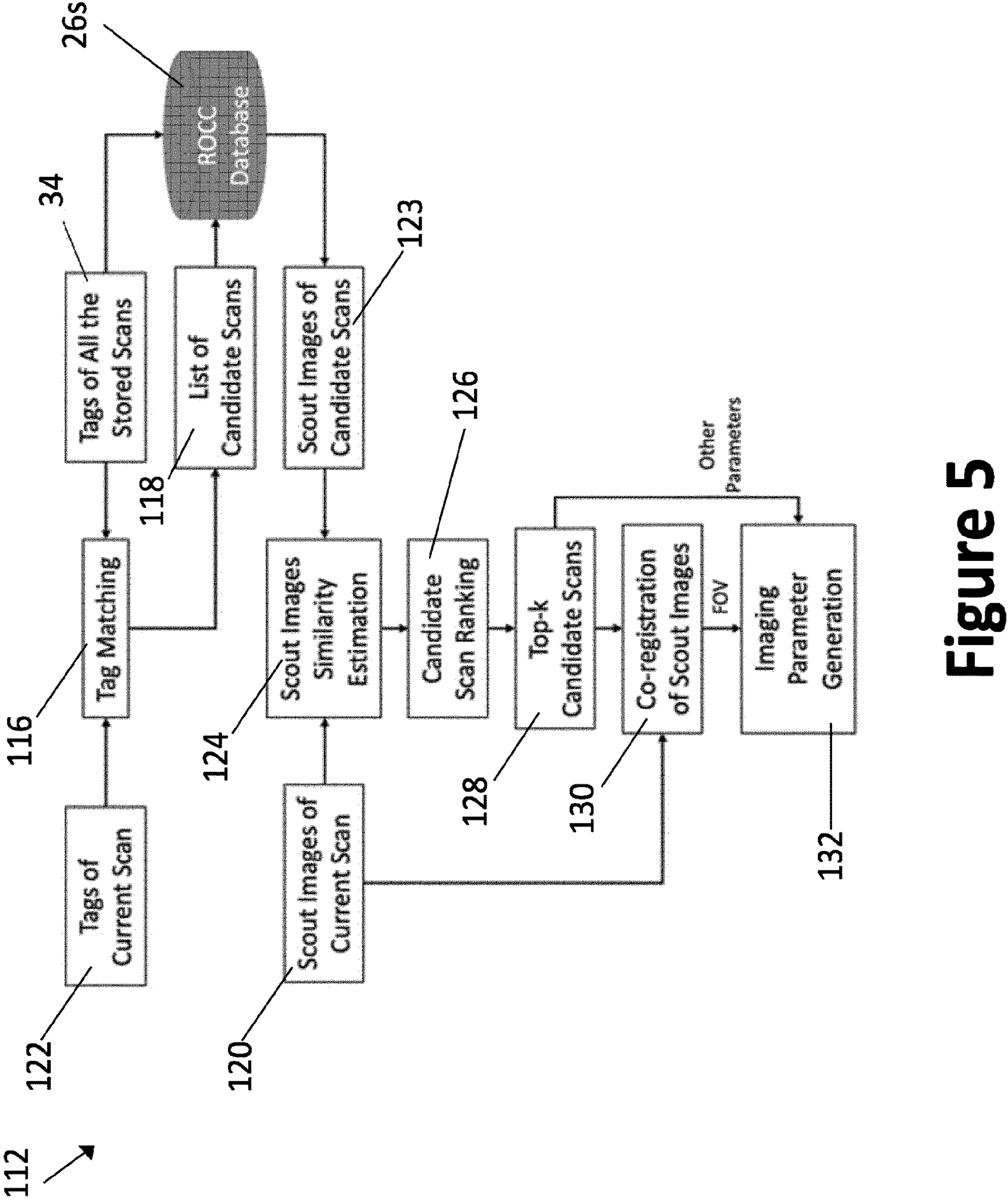
FIG. 5 shows an example flow chart of the operations shown in FIGS. 2 and 3.

At an operation 118, an operator assistance UI 46 is provided on the ROCC device 8, and the suggested scan parameters are displayed on the operator assistance UI 46. With continuing reference to FIGS. 1-3, FIG. 4 shows an example of the display of the scan parameter(s) on the ROCC device 8. In some examples, the suggested scan parameter(s) can be displayed as a plot of different imaging parameter values along a horizontal line of the plot color-coded by the similarity-experience metric (although FIG. 4 is shown in black and white). FIG. 4 shows the suggested scan parameter(s), along with a pre-selected number of scans (e.g., a top 5 scans) selected based on the similarity-experience score. The recommended parameter is indicated by the dot pointed to with the text bubble or call-out. The scout image similarity and the experience level are also shown in the text bubble. The image on the "right" shows the scenario for follow-up scans.

In some embodiments, responsive to an input by the local operator LO (e.g., a finer swipe on the display 36 of the ROCC device 8), a portion of the plot can be selected to display additional information about the medical imaging examination, or the portion of the plot can be selected to display some of the training materials 32 related to the medical imaging examination.

In a particular embodiment, the suggested scan parameter (s) includes a field-of-view (FOV) imaging parameter. With continuing reference to FIGS. 1-3, FIG. 5 diagrammatically shows a flow chart of operations for performing the scan parameter recommendation operation 112 of the method 100 when the scan parameter value to be suggested is a FOV parameter. At an operation 120, one or more initial scans of a patient (i.e., "scout" scans) are acquired with the medical imaging device 2. The scout scan(s) are used as a reference for establishing field-of-view (FOV) markers for subsequent image series. The FOV markers are indicators of the anatomic extent chosen by the local operator LO for an image series and are superimposed on an image prior to the acquisition of that series. The scout scan(s) can be stored in the non-transitory computer readable medium 26*s* of the server computer 14*s*.

For the current medical imaging examination, at an operation 122, the tags 34 can be generated once the information about the current medical imaging scan is extracted from the recorded console videos (e.g., at the operation 102). These tags 34 for the current medical imaging examination can include study type, protocol name, body parts and information about the clinical indication for the study (e.g., whether this is a follow-up scan etc.). The imaging parameters used in each medical imaging examination can also be extracted. Specifically, screenshots showing the setting of the FOV can be extracted. Other parameters used in the medical imaging examination, such as slice thickness, slice overlap, number of slices, in-plane resolution, dose etc. can also be extracted from the screens when the imaging parameters are adjusted.

These screenshots can be used to find similar scans from the non-transitory computer readable medium 26*s*, and to generate a recommended FOV. To do so, at an operation 124, scout scans of candidate scans 123, along with the current scout scans, are input to an artificial neural network (ANN)

48 (implemented in the server computer 14*s*) to detect most similar scans stored in the training database in the non-transitory computer readable medium 26*s*. An experience level of the local operator LO or the remote expert RE performing the medical imaging examination can also be obtained from the non-transitory computer readable medium 26*s*.

At an operation 126, the similarity between the candidate scans 123 and the current scans 120 can be measured with the ANN 48 (i.e., a convolutional neural network (CNN)). This ANN 48 takes a pair of screenshots as input and outputs a similarity score ranges from 0 to 1. Training the CNN model 48 requires manually labelled similarity for pairs of images from the scout scans 120, 123. The initially selected candidate scans can be ranked according to the following similarity-experience score according to Equation 1:

$$S=\alpha*\text{similarity}+\beta*\text{experience\_level}, \quad [1]$$

where α and β are weights to be set based on a preference of the local operator LO, "similarity" is the score output by the CNN 48, and "experience_level" is scaled to the range [0, 1] based on a maximum experience of the technologists and experts who performed the candidate scans. If the current scan is a follow-up scan, the similarity-experience score of the prior scan can be set to the maximum value.

At an operation 128, a top-k similar scans can be determined, where k is chosen by the local operator LO. For the follow-up scans, the parameters used in the prior scan can be recommended. For other scans, the recommended imaging parameters can be generated by averaging of the parameters used in the top-k similar scans, weighted by the similarity-experience score.

At an operation 130, the scout scan images of the top-k similar scans 128 can be spatially registered to those of the current scan 120. The FOV used in the top-k similar scans can be extracted through color and/or intensity filtering, (e.g., typically the boundary of the selected FOV has a different color/intensity than the scout scan images 120).

At an operation 132, FOV corner points of the most similar scans are transformed to a frame-of-reference of the current scan to provide recommended FOV values. The transforming of the FOV to the current scan can be performed with the same transformation matrix determined during the registration operation 130. To get the recommended FOV for the current scan, the coordinates of the corners of the transformed FOV can be averaged, weighted by the similarity-experience score. For a follow-up scan, the FOV used in the prior scan can be transformed to the current scan, without averaging with other similar scans.

Referring back to FIG. 3. for displaying the recommended parameters at the operation 118, the positions of different parameters can be determined from the console screen or from a pre-defined configuration file. The recommended parameters can be overlaid onto the images from the scout scan. For each parameter, the local operator LO can also check the parameters used in the top-k similar scans, together with the final recommended parameter. In that case, each of the top-k similar scans will be shown as a dot with color matching the similarity-experience score. The predicted similarity score and the experience level of each similar scan can also be queried and displayed.

Referring back to FIG. 1, when the local operator LO requires assistance from the remote expert RE, the communication link 14 connects the local operator LO/remote expert RE. The GUI 28 is provided as a remote assistance UI on the display device 24 operable by a remote expert RE. The UI 28 provides two-way communication between the local operator LO and the remote expert RE via which the remote expert can provide assistance to the local medical imaging device operator LO. The remote workstation 12 of the selected remote expert RE, and/or the medical imaging device controller 10 being run by the local operator LO, is configured to perform a method or process 200 for providing assistance from the remote expert RE to the local operator LO. For brevity, the method 200 will be described as being performed by the remote workstation 12. The non-transitory storage medium 26 stores instructions which are readable and executable by the at least one electronic processor 20 (of the workstation 12, as shown, and/or the electronic processor or processors of a server or servers on a local area network or the Internet) to perform disclosed operations including performing the method or process 200.

A suitable implementation of the assistance method or process 200 is as follows. The method 200 is performed over the course of (at least a portion of) a medical imaging examination performed using the medical imaging device 2, and the local expert RE is one selected via the matching method 100. As used herein, the term "duration of a medical imaging examination" (or variants thereof) refers to a time period of a medical imaging examination that includes (i) an actual image acquisition time, (ii) imaging follow-on processing time, and (iii) up to a time of patient release. To perform the method 200, the workstation 12 in the remote location 4 is programmed to receive at least one of: (i) the video 17 from the video camera 16 of the medical imaging device 2 located in the medical imaging device bay 3; and/or (ii) the screen sharing 18 from the screen sharing software 13; and/or (iii) the video 17 tapped by the video cable splitter 15. The video feed 17 and/or the screen sharing 18 can be displayed at the remote workstation display 24, typically in separate windows of the GUI 28. The video feed 17 and/or the screen sharing 18 can be screen-scraped to determine information related to the medical imaging examination (e.g., modality, vendor, anatomy to be imaged, cause of issue to be resolved, and so forth). In particular, the GUI 28 presented on the display 24 of the remote workstation 12 preferably includes a window presenting the video 17, and a window presenting the mirrored screen of the medical imaging device controller 10 constructed from the screen mirroring data stream 18, and status information on the medical imaging examination that is maintained at least in part using the screen-scraped information. This allows the remote operator RE to be aware of the content of the display of the medical imaging device controller 10 (via the shared screen) and also to be aware of the physical situation, e.g., position of the patient in the medical imaging device 2 (via the video 17), and to additionally be aware of the status of the imaging examination as summarized by the status information. During an imaging procedure, the natural language communication pathway 19 is suitably used to allow the local operator LO and the remote operator RE to discuss the procedure and in particular to allow the remote operator to provide advice to the local operator.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

In the foregoing detailed description, for the purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials, and methods that are within the purview of one of ordinary skill in the art are within the scope of the present teachings and may be used in accordance with the representative embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

It will be understood that, although the terms first, second, third, etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only and is not intended to be limiting. As used in the specification and appended claims, the singular forms of terms "a," "an" and "the" are intended to include both singular and plural forms, unless the context clearly dictates otherwise. Additionally, the terms "comprises," "comprising," and/or similar terms specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to," "coupled to," or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

The present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

The invention claimed is:

1. A non-transitory computer readable medium having stored instructions which, when executed by a processor, cause the processor to:

provide a remote assistance user interface (UI) configured for an operator performing a medical imaging examination to receive assistance data from a remote expert user, wherein the remote assistance UI is configured to screen-scape a screen of an imaging device controller used to control an imaging device during the medical imaging examination to acquire data displayed on the screen of the imaging device controller and related to performance of the medical imaging examination;

obtain data related to reference medical imaging examinations during performance of the reference medical imaging examinations;

generate training materials from the obtained data, the training materials related to the performance of the reference medical imaging examinations and scan parameters for the reference medical imaging examinations;

identify one or more scan parameters to control the imaging device during the medical imaging examination based on the acquired data from screen-scraping the screen of the imaging device controller;

generate one or more recommended values for setting the one or more scan parameters to control the imaging device during the medical imaging examination based on recommendations obtained from the training material and the acquired data from screen-scraping the screen of the imaging device controller; and output, through the remote assistance UI, the one or more recommended values for the one or more scan parameters to control the imaging device during the medical imaging examination, wherein the imaging device is controlled in accordance with the one or more scan parameters during the medical imaging examination.

2. The non-transitory computer readable medium of claim 1, wherein the instructions, when executed by the processor, further cause the processor to:

remove personally identifiable information from the obtained data.

3. The non-transitory computer readable medium of claim 1, wherein the instructions, when executed by the processor, further cause the processor to:

tag the training materials with one or more tags generated from the obtained data.

4. The non-transitory computer readable medium of claim 3, wherein the one or more tags include, for a respective reference medical imaging examination of the reference medical imaging examinations, one or more of an identification of a medical imaging device operator who performed the reference medical imaging examination, a modality of the medical imaging device used in performing the reference medical imaging examination, an identification of the medical imaging device used in performing the reference medical imaging examination, an assigned current procedural terminology code for the reference medical imaging examination, an identification of whether assistance from a remote medical expert was used during the reference medical imaging examination, and patient data of a patient examined by the reference medical imaging examination.

5. The non-transitory computer readable medium of claim 3, wherein the obtained data comprises a video stream of the reference medical imaging examinations, and wherein the instructions, when executed by the processor, further cause the processor to:

segment the video stream into a plurality of video stream segments; and tag each video stream segment with one or more tags.

6. The non-transitory computer readable medium of claim 5, wherein, to segment the video stream into a plurality of video stream segments, the instruction, when executed by the processor, further cause the processor to:

segment the video stream based on at least one of a parameter change, sound change, or new step in an imaging protocol.

7. The non-transitory computer readable medium of claim 3, wherein the instructions, when executed by the processor, further cause the processor to:

provide a training materials annotation UI via which an operator performing a reference medical imaging examination of the reference medical imaging examinations tags the training materials obtained during the reference medical imaging examination with the one or more tags.

8. The non-transitory computer readable medium of claim 7, wherein, to provide the training materials annotation UI, the instructions, when executed by the processor, further cause the processor to:

select a portion of the training materials by matching parameters of a current or upcoming medical imaging examination with the tags of the training materials; and transmit, to an operator performing or scheduled to perform the current or upcoming medical imaging examination, a message indicating the selected portion of the training materials to be reviewed based on the matching.

9. The non-transitory computer readable medium of claim 7, wherein, to provide the training materials annotation UI, the instructions, when executed by the processor, further cause the processor to:

receive, from a radiologist reading an imaging examination, a user input indicative of a selection of the imaging examination as a training material; and provide the training materials annotation UI responsive to the user input.

10. The non-transitory computer readable medium of claim 8, wherein the current or upcoming medical imaging examination is a current medical imaging examination; and wherein the training materials are provided to an operator performing the current medical imaging examination during, or prior to, the current medical imaging examination.

11. The non-transitory computer readable medium of claim 1, wherein the instructions, when executed by the processor, further cause the processor to:

determine at least one suggested scan parameter for a current or upcoming medical imaging examination based on the generated training materials; and display the at least one suggested scan parameter to an operator performing or scheduled to perform the current or upcoming medical imaging examination.

12. The non-transitory computer readable medium of claim 1, wherein the instructions, when executed by the processor, further cause the processor to:

generate the training materials from the acquired data from screen-scraping the screen of the imaging device controller, the training materials related to the performance of the reference medical imaging examinations;

retrieve additions to the training materials from a training database, the additions to the training materials including one or more tags corresponding to parameters of the reference medical imaging examinations; and analyze the training materials to identify one or more suggested scan parameters for a current or upcoming medical imaging examination.

13. The non-transitory computer readable medium of claim 12, wherein analysis of the training material includes the instructions, when executed by the processor, further cause the processor to:

compare the tags of the training materials with the scan parameters using a similarity-experience metric for each medical imaging examination.

14. The non-transitory computer readable medium of claim 13, wherein the instructions, when executed by the processor, further cause the processor to determine the similarity-experience metric by:

determining a similarity metric measuring similarity of the current examination to the training materials;

determining an experience level of the operator who performed the examination of the training materials; and multiplying the similarity metric by the experience level.

15. The non-transitory computer readable medium of claim 14, wherein:

the remote assistance UI displays the one or more suggested scan parameters as a plot of different imaging parameter values along a horizontal line of the plot color-coded by the similarity-experience metric.

16. The non-transitory computer readable medium of claim 15, wherein the instructions, when executed by the processor, further cause the processor to:

responsive an input provided by a local operator (LO) via at least one user input device, select a portion of the plot to display additional information about the reference medical imaging examinations.

17. The non-transitory computer readable medium of claim 16, wherein the instructions, when executed by the processor, further cause the processor to:

responsive an input provided by the local operator via at least one user input device, select a portion of the plot to display training materials related to the reference medical imaging examinations.

18. The non-transitory computer readable medium of claim 12, wherein the scan parameter comprises a field-of-view (FOV) imaging parameter; and the instructions, when executed by the processor, further cause the processor to:

acquire one or more scans of a patient using a medical imaging device;

input the one or more scans to an artificial neural network (ANN) to detect most similar scans stored in the training database;

spatially register the most similar scans with the acquired one or more scans; and transform FOV corner points of the most similar scans to a frame-of-reference of a current scan to provide recommended FOV values.

19. The non-transitory computer readable medium of claim 2, wherein the instructions, when executed by the processor, further cause the processor to:

retrieve the training materials from a training database, the training materials including one or more tags corresponding to parameters of the medical imaging examination;

analyze the training materials to identify one or more suggested scan parameters for a current or upcoming medical imaging examination; and provide an operator assistance user interface (UI) on a display operable by an operator performing or scheduled to perform the current or upcoming medical imaging examination, wherein the operator assistance UI displays the one or more suggested scan parameters.

20. The non-transitory computer readable medium of claim 1, wherein the instructions, when executed by the processor, further cause the processor to provide a training user interface (UI) on a display, wherein the training UI displays a visualization of a selected portion of the training materials which is selected based on information about a current or upcoming medical imaging examination.

* * * * *